United States Patent
Liu

(10) Patent No.: US 10,478,386 B2
(45) Date of Patent: Nov. 19, 2019

(54) TWO-PART COSMETIC COMPOSITION FOR CHANGING COLOR OF KERATINIC FIBERS

(71) Applicant: Henkel AG & Co. KGaA, Duesseldorf (DE)

(72) Inventor: Congying Liu, Shanghai (CN)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 15/771,295

(22) PCT Filed: Nov. 27, 2015

(86) PCT No.: PCT/CN2015/095792
§ 371 (c)(1),
(2) Date: Apr. 27, 2018

(87) PCT Pub. No.: WO2017/088175
PCT Pub. Date: Jun. 1, 2017

(65) Prior Publication Data
US 2018/0303728 A1  Oct. 25, 2018

(51) Int. Cl.
| | |
|---|---|
| *A61Q 5/10* | (2006.01) |
| *A61K 8/04* | (2006.01) |
| *A61K 8/73* | (2006.01) |
| *A61K 8/81* | (2006.01) |
| *A61K 8/90* | (2006.01) |

(52) U.S. Cl.
CPC .............. *A61K 8/042* (2013.01); *A61K 8/73* (2013.01); *A61K 8/8147* (2013.01); *A61K 8/8152* (2013.01); *A61K 8/90* (2013.01); *A61Q 5/10* (2013.01); *A61K 2800/4324* (2013.01); *A61K 2800/882* (2013.01)

(58) Field of Classification Search
CPC ................. A61Q 5/10; A61K 2800/88; A61K 2800/4324; A61K 2800/882; A61K 8/73; A61K 8/8147; A61K 8/48; A61K 8/042
See application file for complete search history.

(56) References Cited

U.S. PATENT DOCUMENTS

| 8,882,855 | B2 | 11/2014 | Witte et al. | |
|---|---|---|---|---|
| 2004/0255399 | A1* | 12/2004 | Yang | A61K 8/411 8/405 |
| 2007/0192968 | A1 | 8/2007 | Schmenger | |
| 2013/0220358 | A1* | 8/2013 | Agostino | A61K 8/731 132/208 |
| 2014/0259453 | A1* | 9/2014 | Witte | A61Q 5/10 8/406 |

FOREIGN PATENT DOCUMENTS

| JP | 2005255656 A | 9/2005 |
|---|---|---|
| WO | 03000212 A2 | 1/2003 |
| WO | 2013126657 A2 | 8/2013 |

OTHER PUBLICATIONS

International Cosmetic Ingredient Dictionary and Handbook (Eighth Edition, 2000).
State Intellectual Property Office of the Peoples Republic of China, International Search Report and Written Opinion issued in International Application No. PCT/CN2015/095792, dated Aug. 25, 2016.

* cited by examiner

*Primary Examiner* — Eisa B Elhilo
(74) *Attorney, Agent, or Firm* — Lorenz & Kopf, LLP

(57) ABSTRACT

The present disclosure relates to a two-part cosmetic composition for changing color of keratinic fibers, comprising (a) a gel-like part containing optionally an oxidative dye precursor, and a thickener selected from the group of xanthan gum, anionic amphiphilic polymer, and combination thereof, and (b) an oxidizing part containing an oxidizing agent, and a thickener including one or more anionic amphiphilic polymers.

20 Claims, No Drawings

TWO-PART COSMETIC COMPOSITION FOR CHANGING COLOR OF KERATINIC FIBERS

CROSS-REFERENCE TO RELATED APPLICATION

This application is a U.S. National-Stage entry under 35 U.S.C. § 371 based on International Application No. PCT/CN2015/095792, filed Nov. 27, 2015 which was published under PCT Article 21(2), which is hereby incorporated in their entirety by reference.

TECHNICAL FIELD

The present disclosure relates to a two-part cosmetic composition for changing color of keratinic fibers, to a kit for changing color of keratinic fibers comprising the same, and to a method for changing color of human hair by applying the same.

BACKGROUND

It is well known that the color of keratinous fibers, in particular human hair can be permanently changed by the application of oxidative hair dye and/or dye precursors and suitable oxidizing agents, which diffuse into the hair through the cuticle and into the cortex, in a complex chemical process. There are a large number of constraints in the formulation of the hair coloring products. For example, the products need to meet certain physical parameters in order to ensure that the product can be easily applied to the hair by the consumer to provide the desired effect, without unintentional dripping onto and staining of the skin, clothes, bathroom or hair salon surfaces. Therefore, the hair coloring products are usually designed to make the applied composition have a certain viscosity. This can be achieved by providing the dye composition or the oxidizing composition, preferably the dye composition, as a thickened formulation which thickens the total composition upon mixing. The thickened formulations are highly desirable as they also provide additional benefits of a cream like texture, conditioner like feel and appearance, smooth rinse and improved hair feel. It is also desirable to provide a transparent or clear hair coloring products.

For example, US 20070192968 A discloses a hair coloring product consisting of an agent comprising in a suitable cosmetic carrier a combination of at least one cationic cellulose derivative and at least one polymer selected from the group consisting of acrylamide/ammonium acrylate copolymers and Polyacrylate 13; and a hydrogen peroxide emulsion.

U.S. Pat. No. 8,882,855 B2 discloses a gel-like agent for dyeing keratinic fibers, comprising at least one polymeric thickener selected from homopolymers of acrylic acid or methacrylic acid, copolymers of acrylic acid or methacrylic acid with C1-C4 alkyl esters of acrylic acid or methacrylic acid and combinations thereof.

However, there is still a need for keratinic fibers/hair coloring products with improved easiness of application after the parts of the products are mixed together, meanwhile other needs such as washing fastness on keratinic fibers/hair and cotton cloth are met.

In addition, other objects, desirable features and characteristics will become apparent from the subsequent summary and detailed description, and the appended claims, taken in conjunction with this background.

BRIEF SUMMARY

Based on the foregoing discussion, an object of the present disclosure is to provide a two-part cosmetic composition for changing color of keratinic fibers, comprising,
(a) a gel-like part, comprising,
optionally an oxidative dye precursor, and
a thickener selected from the group of xanthan gum, anionic amphiphilic polymer, and combination thereof, and
(b) an oxidizing part, comprising,
an oxidizing agent, and
a thickener including one or more anionic amphiphilic polymers.

Also provided is a kit for changing color of keratinic fibers, comprising the two-part cosmetic composition for changing color of keratinic fibers, and at least two containers assembled separately from one another, in which a first container holds the gel-like part, and a second container holds the oxidizing part.

Also provided is a method for changing color of human hair by applying the two-part cosmetic composition for changing color of keratinic fibers according to the present disclosure, comprising,
(a) blending the gel-like part with the oxidizing part before application to form a ready-to-use agent;
(b) applying the ready-to-use agent onto the hair;
(c) leaving the ready-to-use agent on the hair for a period of from about 5 to about 45 minutes; and
(d) rinsing the hair with water.

These and other objects, features and advantages of the present disclosure will become better understood upon having reference to the following description of the disclosure.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It is to be understood by one of ordinary skill in the art that the present application is a description of exemplary embodiments only, and is not intended as limiting the broader aspects of the present disclosure.

All percentages listed in this specification are percentages of components by weight, unless otherwise specifically mentioned.

As used in the present specification and in the appended claims, the term "keratinic fibers," "keratin fibers," and similar terminology are understood to mean furs, wool, feathers, and particularly human hair. Although the agents according to the present specification are primarily suitable for changing the color of or dyeing keratin fibers, in principle nothing prevents their use in other fields.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin, in particular the color of human hair.

In one aspect, the present disclosure is directed to a two-part cosmetic composition for changing color of keratinic fibers, comprising, (a) a gel-like part, comprising,
optionally an oxidative dye precursor, and
a thickener selected from the group of xanthan gum, anionic amphiphilic polymer, and combination thereof, and
(b) an oxidizing part, comprising,
an oxidizing agent, and
a thickener comprising one or more anionic amphiphilic polymers.

The combined use of the specific thickeners in the gel-like part and the oxidizing part provides a remarkable performance of the ready-to-use product of hair coloring gel in easiness of application and mixing homogeneity after the two parts are mixed together.

Gel-Like Part

According to the present disclosure, the gel-like part comprises optionally an oxidative dye precursor, and a thickener selected from the group of xanthan gum, anionic amphiphilic polymer, and combination thereof.

In one embodiment, the gel-like part contains the thickener but no oxidative dye precursor. The changing of hair color is achieved by the oxidizing agent comprised in the develop part when it is mixed with the gel-like part, applied onto the hair, diffuse into the hair through the cuticle and into the cortex in a suitable pH range.

In another and preferred embodiment, the gel-like part contains an oxidative dye precursor and the thickener.

The gel-like part includes at least one oxidation dye precursor. The oxidation dye precursor according to the present specification preferably includes at least one oxidation dye precursor of the developer type and at least one oxidation dye precursor of the coupler type.

The developer and coupler components may be employed in free form. For substances with amino groups, it may, however, be preferred to employ them in salt form, especially in the form of the hydrochlorides and hydrobromides or sulfates. Here, developer components and coupler components may be used in approximately molar amounts relative to one another. Although the molar use has also proven to be expedient, a certain excess of individual oxidation dye precursors is not disadvantageous, such that developer components and coupler components may be included in a molar ratio of from about 1:0.5 to about 1:2.

Preferred developer components are selected from p-phenylenediamine, p-toluylenediamine, 2-(2-hydroxyethyl)-p-phenylenediamine, 2-(1,2-dihydroxyethyl)-p-phenylenediamine, N,N-bis-(2-hydroxy-ethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropane-2-ol, bis-(2-hydroxy-5-aminophenyl)methane, 1,3-bis-(2,5-diaminophenoxy)propane-2-ol, N,N'-bis-(4-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)-pyrazole, 2,4,5,6-tetraaminopyrimidine, 4-hydroxy-2,5,6-triaminopyrimidine, 2-hydroxy-4,5,6-triaminopyrimidine, 2,3-diamino-6,7-dihydro-1H,5H-pyrazolo[1,2-a]pyrazol-1-one, as well as the physiologically acceptable salts of these compounds.

Coupler components alone, in the context of the oxidative dyeing, may not form any significant coloration; rather they may be used in the presence of developer components. Therefore it is preferred that when using at least one coupler component, at least one developer component is also used.

Preferred coupler components are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)-ethanol, 1,3-bis(2,4-diaminophenoxy)propane, 1-methoxy-2-amino-4-(2-hydroxyethylamino)-benzene, 1,3-bis(2,4-diaminophenyl)propane, 2,6-bis(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, 4-amino-2-hydroxytoluene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or their physiologically acceptable salts.

In one embodiment, the oxidative dye precursor is selected from the group of p-phenylenediamine hydrochloride, resorcinol, m-aminophenol, 2-methylresorcinol, 2,4-diaminophenoxyethanol dihydrochloride, 1-hydroxyethyl 4,5-diamino pyrazole sulfate, 4-amino-2-hydroxytoluene, and combination thereof.

In one preferred embodiment, the oxidative dye precursor is the combination of p-phenylenediamine hydrochloride, resorcinol, m-aminophenol, 2-methylresorcinol and 2,4-diaminophenoxyethanol dihydrochloride.

In another preferred embodiment, the oxidative dye precursor is the combination of 1-hydroxyethyl 4,5-diamino pyrazole sulfate, m-aminophenol and 4-amino-2-hydroxytoluene.

According to the present disclosure, the oxidative dye precursor is present in an amount of from about 0 to about 15% by weight, preferably from about 0.5% to about 10% by weight, based on the total weight of the gel-like part.

The gel-like part may further include at least one substantive dye as an additional color modifying component for nuancing the coloration. These are dyes that are directly absorbed onto the hair and may not require any oxidative process to develop the color. Examples of substantive dyes include nitrophenylenediamines, nitroaminophenols, azo dyes, anthraquinones or indophenols. The substantive dyes are each preferably employed in quantities of from about 0.001 to about 20.0% by weight, relative to the total end-use preparation. In another embodiment of the present specification, the gel-like part additionally includes at least one substantive dye.

Preferred anionic substantive dyestuffs are compounds known under the international designations or trade names Acid Yellow 1, Acid Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, Bromophenol blue and Tetrabromophenol blue.

Preferred cationic substantive dyes are cationic triphenylmethane dyes, such as for example Basic Blue 7, Basic Blue 26, Basic Violet 2 and Basic Violet 14, aromatic systems that are substituted with a quaternary nitrogen group, such as for example Basic Yellow 57, Basic Red 76, Basic Blue 99, Basic Brown 16 and Basic Brown 17, HC Blue 16 as well as substantive dyes that include a heterocycle that possesses at least one quaternary nitrogen atom, in particular Basic Yellow 16, Basic Orange 87 and Basic Red 31. The cationic substantive dyes that are commercialized under the trade name ARIANOR® are likewise quite particularly preferred cationic substantive dyes.

Non-ionic nitro and quinone dyes and neutral azo dyes are particularly suitable as non-ionic substantive dyes. Preferred non-ionic substantive dyes are the compounds known under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid and 2-chloro-6-ethylamino-4-nitrophenol.

It is not required that each of the oxidation dyestuff precursors or the substantive dyestuffs be pure compounds. In fact, the hair colorants of the present application, due to the manufacturing processes for the individual dyes, may include minor quantities of even more components, in so far as they have no detrimental influence on the coloration result or that they must be excluded on other grounds, e.g. toxicological.

According to the present disclosure, the gel-like part contains a thickener selected from the group of xanthan gum, anionic amphiphilic polymer, and combination thereof.

The anionic amphiphilic polymers are usually polyacrylate or polymethacrylate homopolymers and copolymers, and may be the alkali metal or ammonium salts of such polymers. Illustrative of such polymers may be mentioned, using the chemical nomenclature of the International Cosmetic Ingredient Dictionary and Handbook (Eighth Edition, 2000).

The preferred examples of the anionic amphiphilic polymers used in the gel-like part of present disclosure include, but not limited to (listed as INCI names) PEG-150/Decyl Alcohol/SMDI Copolymer, PEG-150/Stearyl Alcohol/SMDI Copolymer, Acrylates Copolymer, Acrylates/Vinyl Neodecanoate Crosspolymer, Acrylates/Beheneth-25 Methacrylate Copolymer, Acrylates/C10-30 Alkyl Acrylate Crosspolymer, Acrylates/Ceteth-20 Methacrylate Copolymer, Acrylates/Ethylhexyl Acrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Steareth-20 Methacrylate Crosspolymer, Acrylates/C10-30 Alkyl Acrylate Crosspolymer, Acrylates/C10-30 Alkyl Acrylates Crosspolymer, and Steareth-10 Allyl Ether/Acrylates Copolymer. The official chemical description of each of these chemical names can be found in the INCI dictionary or at the website (www.ctfa.org).

In one preferred embodiment, the anionic amphiphilic polymer in the gel-like part is selected from the group of PEG-150/Decyl Alcohol/SMDI Copolymer, PEG-150/Stearyl Alcohol/SMDI Copolymer, Acrylates/Vinyl Neodecanoate Crosspolymer, Acrylates/Steareth-20 Methacrylate Crosspolymer, Acrylates/Steareth-20 Methacrylate Copolymer, Acrylates Copolymer, Acrylates/Ceteth-20 Itaconate Copolymer, Acrylates/Steareth-20 Itaconate Copolymer, Acrylates/Beheneth-25 Methacrylate Copolymer, and combinations thereof.

In another preferred embodiment, the thickener in the gel-like part is selected from the group of xanthan gum, Acrylates/Beheneth-25 Methacrylate Copolymer, and combinations thereof.

According to the present disclosure, the thickener is present in an amount of from about 0.5% to about 20% by weight, preferably from about 1% to about 10% by weight, based on the total weight of the gel-like part.

The gel-like part of the two-part cosmetic composition for changing color of keratinic fibers may further comprise additional auxiliaries and additives including, but not limited to alkalizing agent, anti-oxidant, stabilizer, chelating agent, humectant, and conditioning agent, and combinations thereof.

Examples of the alkalizing agent in the gel-like part include alkaline inorganic materials selected from the group of alkaline potassium hydroxide, sodium hydroxide, sodium silicates, and potassium silicates; non-ammonia alkalizing agent selected from the group of monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof; and an alkalizing agent releasing ammonium ions and or ammonia, selected from the group of ammonium chloride, ammonium sulphate, ammonium nitrate, ammonium phosphate, ammonium acetate, ammonium carbonate, ammonium hydrogen carbonate, ammonium carbamate, ammonium hydroxide, ammonium percarbonate salts, ammonia and mixtures thereof.

In one embodiment, the alkalizing agent is present in the gel-like part in an effective amount so that the pH of the gel-like part is from about 8 to about 12, preferably from about 9 to about 11.

Examples of the antioxidant and stabilizer are ascorbic acid, sodium ascorbate, cysteine, cysteine hydrochloride, N-acetylcysteine, reduced glutathione, sodium sulfite, sodium dithionite, and thioglycolate.

Examples of the chelating agent are polycarboxylic acids, nitrogen-containing mono or polycarboxylic acids, especially ethylenediaminetetraacetic acid (EDTA), ethylenediaminedisuccinic acid (EDDS) and nitrilotriacetic acid (NTA), geminal diphosphonic acids, in particular 1-hydroxyethane-1,1-diphosphonic acid (HEDP), amino phosphonic acids such as ethylenediaminetetra(methylenephosphonic acid) (EDTMP), diethylenetriaminepenta(methylenephosphonic acid) (DTPMP), phosphonopolycarboxyic acids such as 2-phosphonobutane-1,2,4-tricarboxylic acid as well as cyclodextrins, alkali metal stannates (sodium stannate), alkali metal pyrophosphates (tetrasodium pyrophosphate, disodium pyrophosphate), alkali metal phosphates (sodium phosphate), phosphoric acid, dipicolinic acid (DPA), salts thereof and derivatives thereof.

Examples of the humectant include ethylene glycol, glycerin, propylene glycol, dipropylene glycol, triethylene glycol, 1,3-propanediol, butylene glycol, and sorbitol. Other suitable humectants include sodium pyroglutamate, N-acetylethanolamine, sodium lactate, isopropanol, polyalkylene glycols of the formula

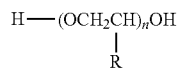

wherein R is H or $CH_3$ and n has an average value of from about 2 to about 10, polyethylene glycol glyceryl ethers, and a variety of other ethoxylated and/or propoxylated chemical agents which are small enough to penetrate hair (e.g. molecular weight of about 500 or less) and enhance its ability to rehydrate. Preferred humectants include glycerin, triethylene glycol, 1,3-propanediol, sodium pyroglutamate, sodium lactate, N-acetyl-ethanolamine and sorbitol.

Examples of conditioning agents include guar hydroxypropyltrimonium chloride, polyquaternium-4 (PQ-4), polyquaternium-5 (PQ-5), polyquaternium-6 (PQ-6), polyquaternium-7 (PQ-7), polyquaternium-22 (PQ-22), polyquaternium-37 (PQ-37), polyquaternium-39 (PQ-39), polyquaternium47 (PQ-47) and polyquaternium-53 (PQ-53).

Oxidizing Part

According to the present disclosure, the oxidizing part of the two-part cosmetic composition for changing color of keratinic fibers comprises an oxidizing agent, and a thickener including one or more anionic amphiphilic polymers.

Preferred oxidizing agents for developing the hair color are water-soluble peroxygen oxidizing agents. "Water-soluble" as defined herein means that in standard condition at least about 0.1 g, preferably about 1 g, more preferably about 10 g of said oxidizing agent can be dissolved in about 1 liter of deionized water. The oxidizing agents are valuable for accelerating the oxidation of the oxidative dye precursors in the hair shaft.

Any oxidizing agent known in the art may be utilized in the present disclosure. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates. etc. Alkyl and aryl peroxides, and or peroxidases may also be used. Mixtures of two or more such oxidizing agents can also be used if desired. The oxidizing agents may be provided in aqueous solution or as a powder which is dissolved prior to use. Preferred for use in the compositions according to the present disclosure are hydrogen peroxide, percarbonate, persulphates, and combinations thereof.

According to the present disclosure, the oxidizing agent is present in an amount of from about 1% to about 20% by weight, preferably from about 3% to about 12% by weight, based on the total weight of the oxidizing part.

Examples of the anionic amphiphilic polymers used in the oxidizing part of present disclosure include, but not limited to (listed as INCI names) PEG-150/Decyl Alcohol/SMDI Copolymer, PEG-150/Stearyl Alcohol/SMDI Copolymer, Acrylates Copolymer, Acrylates/Vinyl Neodecanoate Crosspolymer, Acrylates/Beheneth-25 Methacrylate Copolymer, Acrylates/C10-30 Alkyl Acrylate Crosspolymer, Acrylates/Ceteth-20 Methacrylate Copolymer, Acrylates/Ethylhexyl Acrylate Copolymer, Acrylates/Laureth-25 Methacrylate Copolymer, Acrylates/Palmeth-25 Acrylate Copolymer, Acrylates/Palmeth-25 Itaconate Copolymer, Acrylates/Steareth-50 Acrylate Copolymer, Acrylates/Steareth-20 Itaconate Copolymer, Acrylates/Steareth-20 Methacrylate Copolymer, Acrylates/Steareth-20 Methacrylate Crosspolymer, Acrylates/C10-30 Alkyl Acrylate Crosspolymer, Acrylates/C10-30 Alkyl Acrylates Crosspolymer, and Steareth-10 Allyl Ether/Acrylates Copolymer. The official chemical description of each of these chemical names can be found in the INCI dictionary or at the website (www.ctfa.org).

In one preferred embodiment, the anionic amphiphilic polymer in the oxidizing part is selected from the group of PEG-150/Decyl Alcohol/SMDI Copolymer, PEG-150/Stearyl Alcohol/SMDI Copolymer, Acrylates/Vinyl Neodecanoate Crosspolymer, Acrylates/Steareth-20 Methacrylate Crosspolymer, Acrylates/Steareth-20 Methacrylate Copolymer, Acrylates Copolymer, Acrylates/Ceteth-20 Itaconate Copolymer, Acrylates/Steareth-20 Itaconate Copolymer, Acrylates/Beheneth-25 Methacrylate Copolymer, and combinations thereof.

In another preferred embodiment, the thickener in the gel-like part is Acrylates Copolymers.

According to the present disclosure, the thickener in the oxidizing part is present in an amount of from about 1% to about 20% by weight, preferably from about 1% to about 10% by weight, based on the total weight of the oxidizing part.

The oxidizing part of the two-part cosmetic composition for changing color of keratinic fibers may further comprise additional auxiliaries and additives including, but not limited to alkalizing agent, chelating agent, surfactant, plasticizer, conditioning agent and combination thereof.

Examples of the chelating agent are polycarboxylic acids, nitrogen-containing mono or polycarboxylic acids, especially ethylenediaminetetraacetic acid (EDTA), ethylenediaminedisuccinic acid (EDDS) and nitrilotriacetic acid (NTA), geminal diphosphonic acids, in particular 1-hydroxyethane-1,1-diphosphonic acid (HEDP), amino phosphonic acids such as ethylenediaminetetra(methylenephosphonic acid) (EDTMP), diethylenetriaminepenta(methylenephosphonic acid) (DTPMP), phosphonopolycarboxyic acids such as 2-phosphonobutane-1,2,4-tricarboxylic acid as well as cyclodextrins, alkali metal stannates (sodium stannate), alkali metal pyrophosphates (tetrasodium pyrophosphate, disodium pyrophosphate), alkali metal phosphates (sodium phosphate), phosphoric acid, dipicolinic acid (DPA), salts thereof and derivatives thereof.

Typical surfactants which may be used in oxidizing part include but are not limited to, alkali metal alkyl sulphates (e.g. sodium coco sulfate), alkali metal alkyl ether sulphates (e.g. sodium lauryl ether sulphate (SLES)), sulfosuccinates, acyl glutamates, sultaines, taurates, carboxylates, isethionates, alkyl phosphates, sarcosinates, olefin sulphonates and alkyl polyglucoside esters; alkoxylated alcohols, glyceryl esters (e.g. glyceryl oleate or PEG-7 glyceryl cocoate), glycol esters, alkyl poly glucosides, alkoxylated carboxylic acids, other alkanolamides and their derivatives. Typical non-ionic surfactants include alkoxylated alcohols such as laureth-2, laureth-4, C12/13 pareth-3, ceteareth-4 or oleth-3 or glycol esters such as coconut fatty acid monoglyceride polyglycol ether or modified palm oil polyglycol ether.

Examples of the alkalizing agent used in the oxidizing part include alkaline inorganic materials selected from the group of potassium hydroxide, sodium hydroxide, sodium silicates, and potassium silicates; non-ammonia alkalizing agent selected from the group of monoethanolamine, diethanolamine, triethanolamine, monopropanolamine, dipropanolamine, tripropanolamine, 2-amino-2-methyl-1,3-propanediol, 2-amino-2-methyl-1-propanol, 2-amino-2-hydroxymethyl-1,3-propanediol and mixtures thereof; and an alkalizing agent releasing ammonium ions and or ammonia, selected from the group of ammonium chloride, ammonium sulphate, ammonium nitrate, ammonium phosphate, ammonium acetate, ammonium carbonate, ammonium hydrogen carbonate, ammonium carbamate, ammonium hydroxide, ammonium percarbonate salts, ammonia and mixtures thereof.

In one embodiment, the oxidizing part is present under an acidic condition and the pH value of the oxidizing part is from about 1 to about 5, preferably from about 2 to about 4.

Examples of the conditioning agent include silicones, such as volatile and non-volatile silicones, as for example polyalkylsiloxanes (optionally end-capped with one or more hydroxyl groups), polyalkylaryl siloxanes, siloxane gums and resins, cyclomethicones, aminofunctional silicones, quaternary silicones and mixtures thereof. Preferred silicones include polydimethylsiloxanes (CTFA name dimethicone) (which in the present disclosure are advantageously coupled with a polyethylene glycol such as PEG-12, sold under the trade name Dow Corning 193), siloxane gums, aminofunctional silicones (CTFA name amodimethicone) and hydroxylated polydimethylsiloxanes (CTFA name dimethiconol).

In one embodiment, the gel-like part contains from about 1% to about 3% by weight of PEG-150/Decyl Alcohol/SMDI Copolymer based on the weight of the gel-like part, and the oxidizing part contains from about 1% to about 10% by weight of Acrylates Copolymer based on the weight of the oxidizing part.

In another embodiment, the gel-like part contains from about 1% to about 3% by weight of PEG-150/Decyl Alcohol/SMDI Copolymer based on the weight of the gel-like part, and the oxidizing part contains from about 1% to about 10% by weight of Acrylates/Vinyl Neodecanoate Crosspolymer based on the weight of the oxidizing part.

In yet another embodiment, the gel-like part contains from about 1% to about 3% by weight of xanthan gum based on the weight of the gel-like part, and the oxidizing part contains from about 1% to about 10% by weight of Acrylates Copolymer based on the weight of the oxidizing part.

In yet another embodiment, the gel-like part contains from about 1% to about 3% by weight of Acrylates/Steareth-20 Methacrylate Crosspolymer based on the weight of the gel-like part, and the oxidizing part contains from about 1% to about 10% by weight of Acrylates Copolymer based on the weight of the oxidizing part.

In yet another embodiment, the gel-like part contains from about 1% to about 3% by weight of Acrylates/Steareth-20 Methacrylate Copolymer based on the weight of the gel-like part, and the oxidizing part contains from about 1% to about 10% by weight of Acrylates Copolymer based on the weight of the oxidizing part.

In yet another embodiment, the gel-like part contains from about 1% to about 3% by weight of Acrylates/Steareth-20 Methacrylate Copolymer based on the weight of the gel-like part, and the oxidizing part contains from about 1% to about 10% by weight of Acrylates/Vinyl Neodecanoate Crosspolymer based on the weight of the oxidizing part.

In yet another embodiment, the gel-like part contains from about 1% to about 3% by weight of Acrylates Copolymer based on the weight of the gel-like part, and the oxidizing part contains from about 1% to about 10% by weight of Acrylates Copolymer based on the weight of the oxidizing part.

In yet another embodiment, the gel-like part contains from about 1% to about 3% by weight of Acrylates/Ceteth-20 Itaconate Copolymer based on the weight of the gel-like part, and the oxidizing part contains from about 1% to about 10% by weight of Acrylates Copolymer based on the weight of the oxidizing part.

In yet another embodiment, the gel-like part contains from about 1% to about 3% by weight of Acrylates/Steareth-20 Itaconate Copolymer based on the weight of the gel-like part, and the oxidizing part contains from about 1% to about 10% by weight of Acrylates Copolymer based on the weight of the oxidizing part.

In yet another embodiment, the gel-like part contains from about 1% to about 3% by weight of Acrylates/Beheneth-25 Methacrylate Copolymer based on the weight of the gel-like part, and the oxidizing part contains from about 1% to about 10% by weight of Acrylates Copolymer based on the weight of the oxidizing part.

According to the present disclosure, the gel-like part and the oxidizing part of the two-part cosmetic composition for changing color of keratinic fibers is mixed in a weight ratio of from about 3:1 to about 1:3 so that the viscosity of the ready-to-use agent is suitable to be applied onto hair.

In one embodiment, the viscosity of the ready-to-use agent is from about 1000 to about 200,000 mPa·s, preferably from about 1500 to about 180,000 mPa·s, as measured on a Brookfield viscometer with a Nos. 5-7 spindle at about 4 rpm, and at ambient room temperature. If the viscosity is less than about 1000 mPa·s, the gel layer applied onto the hair will be too thin and may have risk of unintentionally dripping onto and staining other object such as clothes and skin. If the viscosity is larger than about 200,000 mPa·s, the gel preparation will be too thick to easily mix and apply onto the hair.

Surprisingly, the two-part cosmetic compositions for changing color of keratinic fibers contribute to a superior performance profile of the gel preparation obtained by mixing the thickened two parts including a suitable viscosity range to be applied onto hair, an excellent washing fastness, and less staining of skin or other materials after washing.

In another aspect, the present disclosure provides a kit for changing color of keratinic fibers, comprising the two-part cosmetic composition for changing color of keratinic fibers according to the present disclosure, and at least two containers assembled separately from one another, in which a first container holds the gel-like part, and a second container holds the oxidizing part. The contents in the containers are mixed together before use to obtain a ready-to-use agent.

In yet another aspect, the present disclosure provides a method for changing color of human hair by applying the two-part cosmetic composition for changing color of keratinic fibers according to claim 1, comprising, (a) blending the gel-like part with the oxidizing part before application to form a ready-to-use agent, in which, the gel-like part comprises optionally an oxidative dye precursor, and a thickener selected from the group of xanthan gum, anionic amphiphilic polymer, and combinations thereof, and the oxidizing part comprises an oxidizing agent, and a thickener including one or more anionic amphiphilic polymers;

(b) applying the ready-to-use agent onto the hair;

(c) leaving the ready-to-use agent on the hair for a period of from about 5 to about 45 minutes; and (d) rinsing the hair with water.

The present disclosure may be better understood with reference to the following examples.

EXAMPLES

Example 1: Gel-Like Part of a Black Coloring Product without Conditioning Agent A gel-like part of a color gel product changing the hair color to black was prepared according to the formulation as shown in Table 1.

TABLE 1

| Material | Amount (g) | Commercial Source Trade Name | Manufacturer |
|---|---|---|---|
| Group 1 | | | |
| p-Phenylenediamine HCl | 1.93 | p-Phenylenediamine dihydrochloride, purity >99% | Zhejiang Dragon Chemical Co., Ltd. |
| Resorcinol | 0.22 | Resorcinol | Atul Limited |
| m-Aminophenol | 0.1 | 3-Aminophenol, 99% | Zhejiang Dragon Chemical Co., Ltd. |
| 2-Methylresorcinol | 0.18 | 2-Methylresorcinol 99% | Zhejiang Dragon Chemical Co., Ltd. |
| 2,4-Diaminophenoxyethanol 2HCl | 0.06 | 2,4-Diaminophenoxy ethanol 2HCl 99.5% | Zhejiang Dragon Chemical Co., Ltd. |
| Ascorbic acid | 0.2 | Ascorbic Acid | CSPC Weisheng Pharmaceutical |
| Sodium sulfite | 0.4 | Sodium Sulfite Anhy Gran F. G. | Jos H Lowenstein & Sons Inc. |
| EDTA tetrasodium | 0.2 | EDETA BX Powder | BASF SE |
| Propylene glycol | 5.0 | 1,2-Propylenglykol USP | BASF SE |
| Potassium hydroxide | 0.5 | Ätzkali, Plätzchen | PPC SAS |
| Monoethanolamine | 8.0 | Monoethanolamin rein | BASF SE |
| Water, demineralized | 20.0 | — | — |
| Group 2 | | | |
| Acrylates/Beheneth-25 Methacrylate Copolymer | 1.2 | Chromapol 5 polymer | Lubrizol Advanced Materials, Inc. |
| Water, demineralized | added to 100 | — | — |

The materials in Group 1 were mixed at elevated temperature around from about 40 to about 50° C. Then the materials in Group 2 were added into the mixture of Group 1 at room temperature with slow stirring for 5 min until a homogenous gel mixture was obtained.

Example 2: Gel-Like Part of a Black Coloring Product with Conditioning Agent

A gel-like part of a color gel product changing the hair color to black was prepared according to the formulation as shown in Table 1. The gel-like part contains conditioning agents.

TABLE 2

| Material | Amount (g) | Commercial Source Trade Name | Manufacturer |
|---|---|---|---|
| Group 1 | | | |
| p-Phenylenediamine HCl | 1.93 | p-Phenylenediamine dihydrochloride, purity >99% | Zhejiang Dragon Chemical Co., Ltd. |
| Resorcinol | 0.22 | Resorcinol | Atul Limited |
| m-Aminophenol | 0.1 | 3-Aminophenol, 99% | Zhejiang Dragon Chemical Co., Ltd. |
| 2-Methylresorcinol | 0.18 | 2-Methylresorcinol 99% | Zhejiang Dragon Chemical Co., Ltd. |
| 2,4-Diaminophenoxyethanol 2HCl | 0.06 | 2,4-Diaminophenoxy ethanol 2HCl 99.5% | Zhejiang Dragon Chemical Co., Ltd. |
| Ascorbic acid | 0.2 | Ascorbic Acid | CSPC Weisheng Pharmaceutical |
| Sodium sulfite | 0.4 | Sodium Sulfite Anhy Gran F. G. | Jos H Lowenstein & Sons Inc. |
| EDTA tetrasodium | 0.2 | EDETA BX Powder | BASF SE |
| Propylene glycol | 5.0 | 1,2-Propylenglykol USP | BASF SE |

TABLE 2-continued

| Material | Amount (g) | Commercial Source Trade Name | Manufacturer |
|---|---|---|---|
| Potassium hydroxide | 0.5 | Ätzkali, Plätzchen | PPC SAS |
| Monoethanolamine | 8.0 | Monoethanolamin rein | BASF SE |
| Water, demineralized | 20.0 | — | — |
| Group 2 | | | |
| PQ-22 | 3.0 | Merquat 281 (Art. 1106461) | Lubrizol Advanced Materials, Inc. |
| PEG-12 Dimethicone | 1.0 | Xiameter OFX-0193 Fluid | Dow Corning Corp |
| Group 3 | | | |
| Acrylates/Beheneth-25 Methacrylate Copolymer | 1.2 | Chromapol 5 polymer | Lubrizol Advanced Materials, Inc. |
| Water, demineralized | added to 100 | — | — |

The materials in Group 1 were mixed at elevated temperature around from about 40 to about 50° C. Then the materials in Group 3 were added into the mixture of Group 1 at room temperature with slow stirring for 5 min. Then materials in Group 2 were added into the mixture at room temperature with slow stirring until a homogenous gel mixture was obtained.

Example 3: Gel-Like Part of a Red Coloring Product without Conditioning Agent A gel-like part of a coloring gel product changing the hair color to intense red was prepared according to the formulation as shown in Table 3.

The materials in Group 1 were mixed at elevated temperature around from about 40 to about 50° C. Subsequently the materials in Group 2 were added into the mixture of Group 1 at room temperature with slow stirring for 5 min until a homogenous gel mixture was obtained.

Example 4: Gel-Like Part of a Red Coloring Product with Conditioning Agent

A gel-like part of a coloring gel product changing the hair color to intense red was prepared according to the formulation as shown in Table 3. The gel-like part contains conditioning agents.

TABLE 3

| Material | Amount (g) | Commercial Source Trade Name | Manufacturer |
|---|---|---|---|
| Group 1 | | | |
| 1-Hydroxyethyl 4,5-Diamino Pyrazole Sulfate | 1.76 | Pyrazole DHE 99% min. | Zhejiang Dragon Chemical Co., Ltd. |
| m-Aminophenol | 0.4 | 3-Aminophenol, 99% | Zhejiang Dragon Chemical Co., Ltd. |
| 4-Amino-2-Hydroxytoluene | 0.44 | 4-Amino-2-Hydroxy Toluene 99% min. | Zhejiang Dragon Chemical Co., Ltd. |
| Ascorbic acid | 0.2 | Ascorbic Acid | CSPC Weisheng Pharmaceutical |
| Sodium sulfite | 0.4 | Sodium Sulfite Anhy Gran F. G. | Jos H Lowenstein & Sons Inc |
| EDTA tetrasodium | 0.2 | EDETA BX Powder | BASF SE |
| Propylene glycol | 5.0 | 1,2-Propylenglykol USP | BASF SE |
| Potassium hydroxide | 0.5 | Ätzkali, Plätzchen | PPC SAS |
| Monoethanolamine | 10.0 | Monoethanolamin rein | BASF SE |
| Water, demineralized | 20.0 | — | — |
| Group 2 | | | |
| Acrylates/Beheneth-25 Methacrylate Copolymer | 1.2 | Chromapol 5 polymer | Lubrizol Advanced Materials, Inc |
| Water, demineralized | added to 100 | — | — |

TABLE 4

| Material | Amount (g) | Trade Name | Manufacturer |
|---|---|---|---|
| Group 1 | | | |
| 1-Hydroxyethyl 4,5-Diamino Pyrazole Sulfate | 1.76 | Pyrazole DHE 99% min. | Zhejiang Dragon Chemical Co., Ltd. |
| m-Aminophenol | 0.4 | 3-Aminophenol, 99% | Zhejiang Dragon Chemical Co., Ltd. |
| 4-Amino-2-Hydroxytoluene | 0.44 | 4-Amino-2-Hydroxy Toluene 99% min. | Zhejiang Dragon Chemical Co., Ltd. |
| Ascorbic acid | 0.2 | Ascorbic Acid | CSPC Weisheng Pharmaceutical |
| Sodium sulfite | 0.4 | Sodium Sulfite Anhy Gran F. G. | Jos H Lowenstein & Sons Inc |
| EDTA tetrasodium | 0.2 | EDETA BX Powder | BASF SE |
| Propylene glycol | 5 | 1,2-Propylenglykol USP | BASF SE |
| Potassium hydroxide | 0.5 | Ätzkali, Plätzchen | PPC SAS |
| Monoethanolamine | 10 | Monoethanolamin rein | BASF SE |
| Water, demineralized | 20 | — | — |
| Group 2 | | | |
| PQ-22 | 0.5 | Merquat 281 (Art. 1106461) | Lubrizol Advanced Materials, Inc |
| PEG-12 Dimethicone | 0.5 | Xiameter OFX-0193 Fluid | Dow Corning Corp |
| Group 3 | | | |
| Acrylates/Beheneth-25 Methacrylate Copolymer | 1.2 | Chromapol 5 polymer | Lubrizol Advanced Materials, Inc |
| Water, demineralized | added to 100 | — | — |

The materials in Group 1 were mixed at elevated temperature around from about 40 to about 50° C. Subsequently the materials in Group 3 were added into the mixture of Group 1 at room temperature with slow stirring for 5 min. Then materials in Group 2 were added into the mixture at room temperature with slow stirring until a homogenous gel mixture was obtained.

Example 5: True Color Gel-Like Part

A gel-like part of a coloring gel product changing the hair color to natural light brown/dark blonde was prepared according to the formulation as shown in Table 5. The gel-like part contains no oxidative dye precursor.

TABLE 5

| Material | Amount (g) | Trade Name | Manufacturer |
|---|---|---|---|
| Group 1 | | | |
| Ascorbic acid | 0.2 | Ascorbic Acid | CSPC Weisheng Pharmaceutical |
| Sodium sulfite | 0.4 | Sodium Sulfite Anhy Gran F. G. | Jos H Lowenstein & Sons Inc |
| EDTA tetrasodium | 0.2 | EDETA BX Powder | BASF SE |
| Propylene glycol | 5 | 1,2-Propylenglykol USP | BASF SE |
| Potassium hydroxide | 0.5 | Ätzkali, Plätzchen | PPC SAS |
| Monoethanolamine | 10 | Monoethanolamin rein | BASF SE |
| Water, demineralized | 20 | — | — |
| Group 2 | | | |
| PQ-22 | 0.5 | Merquat 281 (Art. 1106461) | Lubrizol Advanced Materials, Inc |
| PEG-12 Dimethicone | 0.5 | Xiameter OFX-0193 Fluid | Dow Corning Corp |
| Group 3 | | | |
| Acrylates/Beheneth-25 Methacrylate Copolymer | 1.2 | Chromapol 5 polymer | Lubrizol Advanced Materials, Inc |
| Water, demineralized | added to 100 | — | — |

The materials in Group 1 were mixed at elevated temperature around from about 40 to about 50° C. Subsequently the materials in Group 3 were added into the mixture of Group 1 at room temperature with slow stirring for 5 min. Then materials in Group 2 were added into the mixture at room temperature with slow stirring until a homogenous gel mixture was obtained.

Examples 6 to 15: Other Gel-Like Parts

The gel-like parts of Examples 6 to 15 have the same compositions as Example 1, except for using specific amount of thickeners shown in Table 6 and balanced water.

TABLE 6

| Example | Thickener | Amount (g) | Commercial Source | |
|---|---|---|---|---|
| | | | Trade Name | Manufacturer |
| Example 6 | PEG-150/Decyl Alcohol/SMDI Copolymer | 1 | Aculyn 44 | Dow Chemical |
| Example 7 | | 3 | | |
| Example 8 | Xanthan Gum | 2 | KELTROL CG-SFT | CP Kelco Germany GmbH |
| Example 9 | Acrylates/Steareth-20 Methacrylate Crosspolymer | 2 | Aculyn 88 | Dow Chemical |
| Example 10 | Acrylates/Steareth-20 Methacrylate Copolymer | 1 | Aculyn 22 | Dow Chemical |
| Example 11 | | 1.5 | | |
| Example 12 | | 3 | | |
| Example 13 | Acrylates Copolymer | 2 | Aculyn 33 | Dow Chemical |
| Example 14 | Acrylates/Ceteth-20 Itaconate Copolymer | 2 | STRUCTURE® 3001 | Akzo Nobel Polymer Chemicals BV |
| Example 15 | Acrylates/Steareth-20 Itaconate Copolymer | 2 | STRUCTURE® 2001 | Akzo Nobel Polymer Chemicals BV |

Example 16: Oxidizing Part

An oxidizing part of a coloring gel product changing the hair color was prepared according to the formulation as shown in Table 7.

TABLE 7

| Material | Amount (g) | Commercial Source | |
|---|---|---|---|
| | | Trade Name | Manufacturer |
| Group 1 | | | |
| Sodium lauryl ether sulphate (27%) | 2 | Texapon NSO UP | BASF SE |
| Acrylates Copolymer | 3.36 | Aculyn 33 | Dow Chemical |
| Group 2 | | | |
| Hydrogen Peroxide | 6 | Cosmetic Grade 50% $H_2O_2$ | Evonik Degussa GmbH |
| PEG-12 Dimethicone | 0.5 | Xiameter OFX-0193 Fluid | Dow Corning Corp |
| Group 3 | | | |
| Dipicolinic acid | 0.1 | Dipicolinsaure | Merck KGaA |
| Disodium pyrophosphate | 0.03 | Saures Natriumpyrophosphat SAPP 28 Pulver, FCC, N 54-88 | Chemische Fabrik Budenheim KG |
| HEDP | 0.2 | Briquest ADPA-60A | Rhodia HPCII SAS |
| Sodium hydroxide | 0.3 | Ätzkali, Plätzchen | PPC SAS |
| Water, demineralized | added to 100 | — | — |

The materials in Group 3 were mixed at elevated temperature around from about 40 to about 50° C. Subsequently the materials in Group 1 were added into the mixture of Group 3 at room temperature with slow stirring for 5 min. Then materials in Group 2 were added into the mixture at room temperature with slow stirring until a homogenous gel mixture was obtained.

Examples 17 to 32: Other Oxidizing Parts

The oxidizing parts of Examples 17 to 32 have the same compositions as Example 16, except for using specific amount of thickeners shown in Table 8 and balanced water.

TABLE 8

| Example No. | Thickener | Amount (g) | Commercial Source Trade Name | Manufacturer |
|---|---|---|---|---|
| Example 17 | Acrylates Copolymer | 1 | Aculyn 33 | Dow Chemical |
| Example 18 | | 10 | | |
| Example 19 | Acrylates/ Steareth-20 Methacrylate Copolymer | 1 | Aculyn 22 | Dow Chemical |
| Example 20 | Acrylates/ Beheneth-2 5 Methacrylate Copolymer | 1 | Chromapol 5 polymer | Lubrizol |
| Example 21 | | 3.36 | | |
| Example 22 | | 10 | | |
| Example 23 | Acrylates/Vinyl Neodecanoate Crosspolymer | 1 | Aculyn 38 | Dow Chemical |
| Example 24 | | 3.36 | | |
| Example 25 | | 10 | | |
| Example 26 | Acrylates/ Steareth-20 Methacrylate Crosspolymer | 1 | Aculyn 88 | Dow Chemical |
| Example 27 | | 3.36 | | |
| Example 28 | | 10 | | |
| Example 29 | PEG-150/Decyl Alcohol/SMDI Copolymer | 1 | Aculyn 44 | Dow Chemical |
| Example 30 | | 3.36 | | |
| Example 31 | | 10 | | |
| Example 32 | PEG-150/Stearyl Alcohol/SMDI Copolymer | 10 | Aculyn 46N | Dow Chemical |

Evaluation:
Viscosity Test

To measure the viscosity of the ready-to-use gel agents, the gel-like parts of Examples 1 to 15 and the oxidizing parts of Examples 16 to 28 were mixed together by selection. Gel-like parts and oxidizing parts were measured by balancer, then added into a glass baker, and mixed by rabble until homogenized. The mixing ratio by weight of the gel-like part to the oxidizing part is 1:1 as in Table 9 and 1:2 as in Table 10.

The viscosity was measured by Brookfield rotating spindle method (all viscosity measurements reported herein are conducted by the Brookfield method whether mentioned or not). The viscosity measurements are calculated in mPa·s, employing a Brookfield rotating spindle viscometer, Model RVT (Brookfield Engineering Laboratories, Inc.), at about 4 revolutions per minute (rpm), at ambient room temperature of from about 20 to about 25° C. Spindle sizes were selected in accordance with the standard operating recommendations from the manufacturer. Generally, spindle sizes were selected as follows:

| Spindle Size No. | Viscosity Range (mPa · s) |
|---|---|
| 1 | 1-50 |
| 2 | 500-1,000 |
| 3 | 1,000-5,000 |
| 4 | 5,000-10,000 |
| 5 | 10,000-20,000 |
| 6 | 20,000-50,000 |
| 7 | >50,000 |

The spindle size recommendations are for illustrative purposes only. A person skilled in the art will select a spindle size appropriate for the system to be measured.

TABLE 9 weight ratio of the gel-like part to the oxidizing part = 1:1

| Gel-like part | Oxidizing part | Viscosity (mPa · s) |
|---|---|---|
| Example 1 | Example 17 | 6850 |
| Example 1 | Example 16 | 23800 |
| Example 1 | Example 18 | 80250 |
| Example 1 | Example 19 | 39550 |
| Example 1 | Example 20 | 24000 |
| Example 1 | Example 23 | 21250 |
| Example 1 | Example 24 | 121000 |
| Example 1 | Example 25 | 170000 |
| Example 1 | Example 26 | 22900 |
| Example 1 | Example 27 | 198000 |
| Example 1 | Example 29 | 10300 |
| Example 1 | Example 30 | 55000 |
| Example 1 | Example 31 | 55250 |
| Example 6 | Example 16 | 3575 |
| Example 6 | Example 18 | 61500 |
| Example 6 | Example 25 | 102000 |
| Example 7 | Example 16 | 15800 |
| Example 8 | Example 17 | 14950 |
| Example 9 | Example 17 | 2800 |
| Example 10 | Example 16 | 10500 |
| Example 10 | Example 23 | 10500 |
| Example 11 | Example 16 | 23500 |
| Example 12 | Example 16 | 56900 |
| Example 12 | Example 25 | 14000 |
| Example 13 | Example 16 | 1725 |
| Example 14 | Example 16 | 7700 |
| Example 15 | Example 16 | 21400 |

TABLE 10 weight ratio of the gel-like part to the oxidizing part = 1:2

| Gel-like part | Oxidizing part | Viscosity (mPa · s) |
|---|---|---|
| Example 1 | Example 18 | 74500 |
| Example 1 | Example 21 | 26000 |
| Example 1 | Example 22 | 18750 |
| Example 1 | Example 23 | 3650 |
| Example 1 | Example 25 | 166000 |
| Example 1 | Example 28 | 18200 |
| Example 1 | Example 31 | 3700 |
| Example 6 | Example 16 | 8000 |
| Example 6 | Example 18 | 77000 |
| Example 6 | Example 32 | 2000 |
| Example 12 | Example 16 | 13200 |

As can be seen in Tables 8 and 9, the combination of the thickeners both in the gel-like part and oxidizing part of the hair coloring composition according to the present disclosure contributed to a suitable range of viscosity of from about 1000 to about 200000 mPa·s, which allowed the ready-to-use gel agent to be easily applied on the hair and did not tend to drip onto other objects such as skin and clothes.

Miscibility Test

The following process was applied to determine the miscibility of the ready-to-use gel agents:

Each gel-like part was prepared according to composition and method mentioned above, except that Hydrophobic dye (HC Blue No. 1) was added into the gel-like part in a concentration of 0.001% by weight of the gel-like part;

Each oxidizing part was prepared according to composition and method mentioned above, except that hydrogen peroxide was not added as hydrophobic dyes would fade if it contacted with hydrogen peroxide;

50 g of the gel-like part and 50 g of the oxidizing part were added into 200 ml volume plastic bottle;

Shake the contents of the bottle to mix. Visually check if the contents well mixed in every 3 shakes. If it is well mixed, the mixture will appear to be blue; and The miscibility of the ready-to-use gel agent was subjected to a sensory test, in which miscibility performance was sensorially scored according to the following scoring criteria. In the scoring criteria, a higher score means a better miscibility and improved easiness of use.

Score Criteria:
5: well mixed after 3 shakes
4: well mixed after 6 shakes
3: well mixed after 9 shakes
2: well mixed after 12 shakes
1: well mixed after >12 shakes The test results are shown in Table 11.

TABLE 11

| Gel-like part | Oxidizing part | Score |
|---|---|---|
| Example 7 | Example 16 | 5 |
| Example 7 | Xanthan Gum | 4 |
| Example 11 | Example 16 | 5 |
| Example 11 | Example 22 | 5 |
| Example 11 | Example 25 | 5 |
| Example 11 | Xanthan Gum | 4 |
| Example 12 | Example 22 | 4 |
| Example 12 | Xanthan Gum | 3 |
| Example 1 | Example 16 | 5 |
| Example 1 | Example 22 | 5 |
| Example 1 | Example 25 | 5 |
| Example 1 | Xanthan Gum | 4 |

As is evident from the result in Table 11, the miscibility of the thickened gel-like part and oxidizing part according to the present disclosure is significantly better than that using xanthan gum as the thickener in the oxidizing part.

It is believed that the anionic amphiphilic polymers are pH-dependent materials, and possessed lower viscosity under acidic condition, for example pH of from about 2 to about 4 in the oxidizing part of the present compositions, and thus could be more easily mixed with the gel-like part having an alkaline pH value. Upon mixing, the viscosity of the anionic amphiphilic polymers largely increased due to the significant change of pH value. However, it is known that xanthan gum is not a pH-dependent material and thus possessed a higher viscosity than that of anionic amphiphilic polymers under acidic condition, which caused the uneasiness of mixing the oxidizing part containing xanthan gum with gel-like part to homogeneity as demonstrated in the miscibility test.

Washing Fastness Test

The washing fastness of the ready-to-use gel product for hair coloring according to the present disclosure versus commercial products (SK Natural & Easy 3.0 Black; SK Perfect Mouse 3.0 Black; SK Natural & Easy 6.88 and SK Perfect Mouse 688, all commercially available from Schwarzkopf & Henkel) was measured as follows. The compositions of SK Natural & Easy 3.0 Black and SK Perfect Mouse 3.0 Black both contain the oxidative dye precursor and oxidizing agent in same type and same amount as those in Example 2. The compositions of SK Natural & Easy 6.88 and SK Perfect Mouse 688 both contain the oxidative dye precursor and oxidizing agent in same type and same amount as those in Example 4.

All strands (Kerling Asian natural hair (white), length 8 cm, weight 0.8 g, (bag T40)) were pre-cleaned in an ultrasonic bath with a solution of Texapon NSO (≈3% active material, pH 6-7) in water for 5 minutes. Subsequently the strands were rinsed with tap water and dried with a cold blow dry.

The gel-like part and the oxidizing part were mixed in a weight ratio of 1:1 in a plastic container until homogeneity and the ready-to-use gel product was applied to the dry hair. The application ratio is 5 g of coloration mixture per g of hair. The exposure time is 30 min at room temperature. Then the strands were rinsed with tap water for 2 min and dried.

For the evaluation of washing fastness a 2% shampoo solution (Schauma 7-Herbs shampoo) was filled into an ultrasonic bath. The strands to be washed were immersed into this solution up to their bound ends and treated with ultrasound (11 minutes in an ultrasonic bath correlate with 6 hand washings; the washing solution was changed after each washing cycle). All strands were measured after coloration and after 6, 12, 18, 24 and 30 washings at four different measuring points on the strand. Three hair strands were used for each product and the median was calculated for all strands. From the $\Delta E_{00}$ value values measured by Colorimetry (Datacolor Spectraflash SF 450; Light source: D65; Program: Datacolor Tools 2.0.1) the color difference was calculated by the following formula:

$$\Delta E_{00}^* = \sqrt{\left(\frac{\Delta L'}{S_L}\right)^2 + \left(\frac{\Delta C'}{S_C}\right)^2 + \left(\frac{\Delta H'}{S_H}\right)^2 + R_T \frac{\Delta C'}{S_C} \frac{\Delta H'}{S_H}}$$

$$\Delta L' = L_i - L_o$$

$$\Delta C' = C'_0 - C'_i \text{ with } C'_i = \sqrt{a_i'^2 + b_i'^2} \text{ and}$$

$$a_i' = a_i + \frac{a_i}{2}\left(1 - \sqrt{\frac{\overline{C}^7}{\overline{C}^7 + 25^7}}\right)$$

$$(\overline{C} = \text{mean})$$

$$\Delta H = 2\sqrt{C_0'C_1'} \sin(\Delta h'/2)$$

L=lightness, ΔL=lightness difference.
a=red/green, Δa=color difference in red/green
b=yellow/blue, Δb=color difference in yellow/blue.
ΔE=entire color difference
ΔC=difference in chroma or color saturation
ΔH=difference in color direction
$S_L$=weighting coefficients of lightness difference ΔL
$S_c$=weighting coefficients of saturation difference ΔC
$S_H$=weighting coefficients of hue difference ΔH
$R_T$=spectral reflectance
Δh=hue angle difference
$L_i$, $a_i$, $b_i$, $C_i$=value after 6, 12, 18, 24, 30 washings
$L_0$, $a_0$, $b_0$, $C_0$=value of colored and unwashed For the evaluation of washing fastness, the color difference ($\Delta E_{00}$ value) was determined between the unwashed colored and the washed colored strand. A higher $\Delta E_{00}$ value indicates an inferior washing fastness.

The results are shown in Tables 12 and 13.

TABLE 12

| Ready-to-use agent | Gel-like part | Oxidizing part | $\Delta E_{00}$ |
|---|---|---|---|
| Inventive | Example 2 | Example 16 | 1.17 |
| SK Natural & Easy 3.0 Black | — | — | 1.40 |
| SK Perfect Mouse 3.0 Black | — | — | 1.07 |

TABLE 13

| Ready-to-use agent | Gel-like part | Oxidizing part | $\Delta E_{00}$ |
|---|---|---|---|
| Inventive | Example 4 | Example 16 | 4.36 |
| SK Natural & Easy 688 | — | — | 4.31 |
| SK Perfect Mouse 688 | — | — | 3.83 |

As can be seen from the result in Tables 12 and 13, there was no statistical significant difference between the product obtained from the inventive compositions and the commercial products. In other words, the inventive compositions are capable of providing a comparable washing fastness with the commercial products.

Staining Test

Although the ready-to-use agents according to the present disclosure possess a suitable viscosity range for the application onto the hair to be colored, and thus the risk of dripping onto skin or clothes are decreased, the use of the colorant agent is still challenging since it can easily stain other objects if intentionally contacted. Therefore, it is necessary to test the staining property of the agent following the process as below.

The ready-to-use agents were well mixed and then applied to dry cotton cloth. The application ratio is 2 g mixture per 5 cm diameter circle. The exposure time is 20 min at room temperature. Then cotton cloth was rinsed off with 10% sodium laureth sulfate water solution for 30 min, then rinsed off with tap water for 2 min and dried.

$\Delta E_{00}$ value of cotton cloth was measured before application and after dry by Colorimetry (Datacolor Spectraflash SF 450; Light source: D65; Program: Datacolor Tools 2.0.1). The color differences were calculated by the formula which is the same as washing fastness.

The staining property of the ready-to-use gel product for hair coloring according to the present disclosure versus commercial products (SK Natural & Easy 3.0 Black; SK Perfect Mouse 3.0 Black; SK Natural & Easy 6.88 and SK Perfect Mouse 688, all commercially available from Schwarzkopf & Henkel) was measured as follows.

The gel-like part and the oxidizing part were mixed in a weight ratio of 1:1 in a plastic container until homogeneity and 2 g of the ready-to-use gel product was applied to a piece of cotton cloth and held for 20 min. Then the stains on the cotton cloth were rinsed with 10% SLES aqueous solution for 2 min and hanged on to dry.

For the evaluation of staining property, the color difference ($\Delta E_{00}$ value) was determined between the unwashed colored and the washed colored cotton cloth. A higher $\Delta E_{00}$ value indicates an inferior staining property.

The results are shown in Table 14.

TABLE 14

| Ready-to-use agent | Gel-like part | Oxidizing part | $\Delta E_{00}$ |
|---|---|---|---|
| Inventive | Example 2 | Example 16 | 3.99 |
| SK Natural & Easy 3.0 Black | — | — | 6.97 |
| SK Perfect Mouse 3.0 Black | — | — | 6.33 |
| SK Igora 3-0 Black | — | — | 8.33 |

As is evidenced from the result in Table 14, the ready-to-use gel product according to the present disclosure was less staining and easier to rinse off on cotton cloth compared to commercial products.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A two-part cosmetic composition for changing color of keratinic fibers, comprising,
(a) a gel-like part having a pH of from about 8 to about 12 and comprising,
optionally an oxidative dye precursor, and
a thickener selected from the group of xanthan gum, anionic amphiphilic polymer, and combination thereof, and
(b) an oxidizing part having a pH of from about 1 to about 5 comprising,
an oxidizing agent, and
a thickener comprising one or more anionic amphiphilic polymers;
wherein the two-part cosmetic composition has a viscosity of from about 1000 to about 200000 mPa·s measured using a Brookfield rotating spindle viscometer Model RVT at about 4 rpm and from about 20 to about 25° C.

2. The two-part cosmetic composition for changing color of keratinic fibers according to claim 1, wherein the anionic amphiphilic polymer in the gel-like part or oxidizing part is independently selected from the group of PEG-150/Decyl Alcohol/SMDI Copolymer, PEG-150/Stearyl Alcohol/SMDI Copolymer, Acrylates/Vinyl Neodecanoate Crosspolymer, Acrylates/Steareth-20 Methacrylate Crosspolymer, Acrylates/Steareth-20 Methacrylate Copolymer, Acrylates Copolymer, Acrylates/Ceteth-20 Itaconate Copolymer, Acrylates/Steareth-20 Itaconate Copolymer, Acrylates/Beheneth-25 Methacrylate Copolymer, and combinations thereof.

3. The two-part cosmetic composition for changing color of keratinic fibers according to claim 1, wherein the thickener in the gel-like part is selected from the group of PEG-150/Decyl Alcohol/SMDI Copolymer, xanthan gum, Acrylates/Steareth-20 Methacrylate Crosspolymer, Acrylates/Steareth-20 Methacrylate Copolymer, Acrylates Copolymer, Acrylates/Ceteth-20 Itaconate Copolymer, Acrylates/Beheneth-25 Methacrylate Copolymer, and combinations thereof.

4. The two-part cosmetic composition for changing color of keratinic fibers according to claim 1, wherein the thickener in the gel-like part is selected from the group of xanthan gum, Acrylates/Beheneth-25 Methacrylate Copolymer, and combinations thereof.

5. The two-part cosmetic composition for changing color of keratinic fibers according to claim 1, wherein the anionic amphiphilic polymer in the oxidizing part is selected from the group of PEG-150/Decyl Alcohol/SMDI Copolymer, PEG-150/Stearyl Alcohol/SMDI Copolymer, Acrylates/Vinyl Neodecanoate Crosspolymer, Acrylates/Steareth-20 Methacrylate Crosspolymer, Acrylates/Steareth-20 Methacrylate Copolymer, Acrylates Copolymer, Acrylates/Ceteth-20 Itaconate Copolymer, Acrylates/Steareth-20 Itaconate Copolymer, Acrylates/Beheneth-25 Methacrylate Copolymer, and combination thereof.

6. The two-part cosmetic composition for changing color of keratinic fibers according to claim 1, wherein the oxidative dye precursor in the gel-like part is present in an amount of from about 0 to about 15% by weight, based on the total weight of the gel-like part.

7. The two-part cosmetic composition for changing color of keratinic fibers according to claim 1, wherein the thickener in the gel-like part is present in an amount of from about 0.5% to about 20% by weight based on the total weight of the gel-like part.

8. The two-part cosmetic composition for changing color of keratinic fibers according to claim 1, wherein the thickener in the oxidizing part is present in an amount of from about 1% to about 20% by weight, based on the total weight of the oxidizing part.

9. The two-part cosmetic composition for changing color of keratinic fibers according to claim 1, wherein the oxidizing agent is present in an amount of from about 1% to about 20% by weight, based on the total weight of the oxidizing part.

10. The two-part cosmetic composition for changing color of keratinic fibers according to claim 1, wherein the gel-like part or oxidizing part further comprises an additive selected from the group of alkalizing agent, anti-oxidant, stabilizer, chelating agent, humectant, surfactant and conditioning agent, and combination thereof.

11. The two-part cosmetic composition for changing color of keratinic fibers according to claim 1, wherein the gel-like part is mixed with the oxidizing part prior to use.

12. A kit for changing color of keratinic fibers, comprising the two-part cosmetic composition for changing color of keratinic fibers according to claim 1, and at least two containers assembled separately from one another, in which a first container holds the gel-like part, and a second container holds the oxidizing part.

13. A method for changing color of human hair by applying the two-part cosmetic composition for changing color of keratinic fibers according to claim 1, comprising,
(a) blending the gel-like part with the oxidizing part before application to form a ready-to-use agent, in which,
the gel-like part comprises optionally an oxidative dye precursor, and a thickener selected from the group of xanthan gum, anionic amphiphilic polymer, and combination thereof, and
the oxidizing part comprises an oxidizing agent, and a thickener comprising one or more anionic amphiphilic polymers;
(b) applying the ready-to-use agent onto the hair;
(c) leaving the ready-to-use agent on the hair for a period of from about 5 to about 45 minutes; and
(d) rinsing the hair with water.

14. The two-part cosmetic composition for changing color of keratinic fibers according to claim 1, wherein the anionic amphiphilic polymer in the oxidizing part is acrylates copolymers.

15. The two-part cosmetic composition for changing color of keratinic fibers according to claim 1, wherein the oxidative dye precursor in the gel-like part is present in an amount of from about 0.5 to about 10% by weight, based on the total weight of the gel-like part.

16. The two-part cosmetic composition for changing color of keratinic fibers according to claim 1, wherein the thickener in the gel-like part is present in an amount of from about 1% to about 10% by weight based on the total weight of the gel-like part.

17. The two-part cosmetic composition for changing color of keratinic fibers according to claim 1, wherein the thickener in the oxidizing part is present in an amount of from about 1% to about 10% by weight, based on the total weight of the oxidizing part.

18. The two-part cosmetic composition for changing color of keratinic fibers according to claim 1, wherein the anionic amphiphilic polymer in the oxidizing part is acrylates copolymers, wherein the anionic amphiphilic polymer in the gel-like part is selected from the group of PEG-150/Decyl Alcohol/SMDI Copolymer, PEG-150/Stearyl Alcohol/SMDI Copolymer, Acrylates/Vinyl Neodecanoate Crosspolymer, Acrylates/Steareth-20 Methacrylate Crosspolymer, Acrylates/Steareth-20 Methacrylate Copolymer, Acrylates Copolymer, Acrylates/Ceteth-20 Itaconate Copolymer, Acrylates/Steareth-20 Itaconate Copolymer, Acrylates/Beheneth-25 Methacrylate Copolymer, and combinations thereof, wherein the oxidative dye precursor in the gel-like part is present in an amount of from about 0.5 to about 10% by weight, based on the total weight of the gel-like part, wherein the thickener in the gel-like part is selected from the group of xanthan gum, Acrylates/Beheneth-25 Methacrylate Copolymer, and combinations thereof, and is present in an amount of from about 1% to about 10% by weight based on the total weight of the gel-like part, wherein the thickener in the oxidizing part is present in an amount of from about 1% to about 10% by weight, based on the total weight of the oxidizing part, wherein the oxidizing agent is present in an amount of from about 3% to about 12% by weight, based on the total weight of the oxidizing part, wherein the pH of the gel-like part is from about 9 to about 11, and wherein the pH of the oxidizing part is from about 2 to about 4.

19. The two-part cosmetic composition for changing color of keratinic fibers according to claim 1, wherein the oxidizing part is free of xanthan gum.

20. A two-part cosmetic composition for changing color of keratinic fibers, the two-part cosmetic composition comprising:
(a) a gel-like part having a pH of from about 8 to about 12 and comprising,
an oxidative dye precursor, and
a thickener selected from the group of xanthan gum, PEG-150/Decyl Alcohol/SMDI Copolymer, Acrylates/Steareth-20 Methacrylate Crosspolymer, Acrylates/Steareth-20 Methacrylate Copolymer, Acrylates Copolymer, Acrylates/Ceteth-Itaconate Copolymer, Acrylates/Beheneth-25 Methacrylate Copolymer, and combinations thereof;

(b) an oxidizing part having a pH of from about 1 to about 5 and comprising,
 an oxidizing agent, and
 a thickener selected from the group of PEG-150/Decyl Alcohol/SMDI Copolymer, PEG-150/Stearyl Alcohol/SMDI Copolymer, Acrylates/Vinyl Neodecanoate Crosspolymer, Acrylates/Steareth-20 Methacrylate Crosspolymer, Acrylates/Steareth-20 Methacrylate Copolymer, Acrylates Copolymer, Acrylates/Beheneth-25 Methacrylate Copolymer, and combinations thereof,
wherein the two-part cosmetic composition has a viscosity of from about 1000 to about 200000 mPa·s measured using a Brookfield rotating spindle viscometer Model RVT at about 4 rpm and from about 20 to about 25° C.

* * * * *